United States Patent [19]

Portoghese et al.

[11] Patent Number: 5,464,841
[45] Date of Patent: Nov. 7, 1995

[54] USE OF DELTA OPIOID RECEPTOR ANTAGONISTS TO TREAT IMMUNOREGULATORY DISORDERS

[76] Inventors: Philip S. Portoghese, 17 Oriole La., St. Paul, Minn. 55127; Burt M. Sharp, 4301 Cedarwood Rd., St. Louis Park, Minn. 55416; Kristin M. Linner, 831 S. Cleveland Ave., St. Paul, Minn. 55116

[21] Appl. No.: 149,039

[22] Filed: Nov. 8, 1993

[51] Int. Cl.$^6$ .................. A61K 31/445; C07D 221/02; C07D 471/02; C07D 453/00
[52] U.S. Cl. .............. 514/279; 514/305; 546/37; 546/133
[58] Field of Search .................. 514/279, 252, 514/410, 443, 453, 305; 548/417; 549/41, 456; 546/37, 133

[56] References Cited

U.S. PATENT DOCUMENTS

| | | | |
|---|---|---|---|
| 4,816,586 | 3/1989 | Portoghese et al. | 544/340 |
| 5,244,904 | 9/1993 | Nagase et al. | 514/285 |
| 5,332,818 | 7/1994 | Nagase et al. | 546/37 |

FOREIGN PATENT DOCUMENTS 456833  11/1990  European Pat. Off. .

OTHER PUBLICATIONS

T. Akami et al., *Transplantation Proceedings*, 24, 485 (1992).
K. Arakawa et al., "Delta Opioid Receptor Antagonist for Immunosuppression after Rat Kidney Transplantation", Abstract and Poster #18, Fifty–fourth Annual Scientific Meeting of the International Narcotics Research Conference, Jun. 23–27 (1992).
K. Arakawa et al., *Transplantation*, 53, 951 (1992) is cited in the specification at p. 2, line 31.
K. Arakawa, et al., *Transplant*, 24, 696 1992) is cited in the specification at p. 2, line 31.
R. Cotton et al., *Eur. J. Pharmacol.*, 97, 331 (1984) is cited in the specification at p. 1, line 23, p. 2, line 27.
W. E. Crowe et al., *Arth. Rheum.*, 28, 537 (1985) is cited in the specification at p. 3, lines 11 and 23.
*Cytomegalovirus–Biology and Infection*, M. Ho., ed., Plenum, NY (1982) at pp. 223–243 is cited in the specification at p. 10, line 13.
E. C. Ebert et al., *Clin. Immunol. Immunopathol.*, 37, 283 (1985) is cited in the specification at p. 10, line 16.
R. E. Faith et al., *NIDA Res. Monogr.*, 54, 300 (1984) is cited in the specification at p. 2, line 6. (I).
R. E. Faith et al., *Ann. N.Y. Acad. Sci.*, 496, 137 (1987) is cited in the specification at p. 2, line 9. (II).
J. C. Froelich et al., *Alcoholism Clin. and Exp. Res.*, Abstract 20, p. 315 (1991) is cited in the specification at p. 1, line 31.
S. Gupta et al., *Vox Sang.*, 44, 265 1983) is cited in the specification at p. 10, lines 6, 9 and 10.
J. K. Gutowski et al., *Immunol.* 46, 801 (1982) is cited in the specification at p. 11, lines 1 and 3.
D. A. Hafler et al., *Clin. Immunol. and Immunopathol.*, 58, 115 (1991) is cited in the specification at p. 10, line 7 and 35.
D. A. Hafler et al., *Immunol. Today*, 10, 104 (1989) is cited in the specification at p. 10, line 20.
T. Han et al., *Blood*, 60, 1075 (1982) is cited in the specification at p. 10, line 18.
R. L. Hirsch, *Clin. Exp. Immunol.*, 64, 107 (1986) is cited in the specification at p. 3, line 22 and at p. 10, line 4.
M. Hendrickson et al., *Journal of Burn Care and Rehabilitation*, 10, 494 (1989).

(List continued on next page.)

Primary Examiner—Glennon H. Hollrah
Assistant Examiner—Deborah Lambkin

[57] ABSTRACT

A therapeutic method is provided to elevate a depressed mammalian autologous mixed lymphocyte response and to alleviate the diseases associated therewith by the administration of an effective amount of certain selective delta opioid receptor antagonists to a mammal such as a human patient in need of such treatment.

15 Claims, 6 Drawing Sheets

OTHER PUBLICATIONS

B. D. Jankovic et al., *Ann. N.Y. Acad. Sci.*, 540, 691 (1988) is cited in the specification at p. 2, line 26.

D. Kelleher et al., *Gut*, 30, 839 (1989) is cited in the specification at p. 10, line 35.

M. M. Kuntz et al., *J. Exp. Med.*, 143, 1042 (1976) is cited in the specification at p. 3, line 14.

A. Laffon et al., *Rheumatol. Int.*, 3, 117 (1983) is cited in the specification at p. 10, line 5 and p. 11, line 12.

D. Maric et al., *Ann. N.Y. Acad. Sci.* 496 126 (1987) is cited in the specification at p. 2, line 13.

W. R. Martin, *Pharmacol. Rev.*, 35, 283 (1983) is cited in the specification at p. 1, line 14.

D. R. Oleson et al., *Brain, Behavior and Immun.*, 2, 171 (1988) is cited in the specification at p. 2, line 14.

Prakash et al., *Cell. Immunol.*, 112, 64 1988) is cited in the specification at p. 11, line 1.

P. S. Portoghese et al., *J. Med. Chem.*, 31, 281 (1988) is cited in the specification at p. 5, lines 3 and 7.

P. S. Portoghese et al., *J. Med. Chem.*, 33, 1547 (1990) is cited in the specification at p. 5, line 6.

P. S. Portoghese et al., *Eur. J. Pharmacol.*, 146, 185 (1988) is cited in the specification at p. 5, line 7.

Abdelhamin et al. *J. Pharmacol. Exp. Ther.*, 258, 299 (1991) is cited in the specification at p. 5, line 8.

J. W. Shaw et al., *Life Sci.*, 31, 1259 (1982) is cited in the specification at p. 1, line 22.

J. S. Smolen et al., *J. Clin. Invest.*, 68, 1601 (1981) is cited in the specification at p. 3, line 16.

M. Sofouglu et al., *J. Pharmacol. Exp. Ther.*, 257, 676 (1991) is cited in the specification at p. 1, line 32.

N. Talal et al., *Behring Inst. Mitt.*, 72, 169 (1983) is cited in the specification at p. 12, line 3.

D. D. Taub et al., *PNAS USA*, 88, 360 (1991).

M. E. Weksler et al., *J. Exp. Med.*, 146, 1833 (1977) is cited in the specification at p. 3, line 15.

J. Wybran et al., *J. Immunol.*, 123, 1068 (1979) is cited in the specification at p. 2, line 5.

USE OF DELTA OPIOID RECEPTOR ANTAGONISTS TO TREAT IMMUNOREGULATORY DISORDERS

BACKGROUND OF THE INVENTION

The fact that the effects of endogenous opioid peptides, such as the enkephalins, and exogenous opiates such as morphine, are mediated by at least three different types [mu (μ), delta (δ), kappa (κ)] of opioid receptors raises the possibility that highly selective exogenous opioid agonists or antagonists might be developed. See W. R. Martin, *Pharmacol. Rev.*, 35, 283 (1983). In fact, in recent years, some progress has been made in the development of selective opioid antagonists. Pentapeptides structurally related to the enkephalins have been reported to be highly delta-selective opioid antagonists. Such compounds (e.g., ICI 174864) currently are employed as pharmacologic probes of receptor function and structure, but they possess the disadvantage of low potency and poor penetration into the central nervous system (CNS). See J. W. Shaw et al., *Life Sci.*, 31, 1259 (1982) and R. Cotton et al., *Eur. J. Pharmacol.*, 97, 331 (1984). Portoghese et al. (U.S. Pat. No. 4,816,586) disclose certain opiate analogs which possess high selectivity and potency at delta receptors, including naltrindole (NTI) and 7-benzylidene-naltrexone (BNTX). Certain of these compounds have been reported both to deter ethanol ingestion in an alcohol-preferring rat line and to block morphine tolerance and dependence in the rat model. See, J. C. Froehlich et al., *Alcoholism Clin. and Exp. Les.*, Abstract 20, page 315 (1991) and M. Sofuoglu et al., *J. Pharmacol. Exp. Ther.*, 257, 676 (1991).

In recent years, it has also been shown that endogenous opioid peptides and exogenous opiates modulate immune responses both in vitro and in vivo. The enkephalins, for example, have been shown to enhance the expression of CD2 molecules on T lymphocytes both in normal individuals and immunosuppressed patients. See, for example, J. Wybran et al., *J. Immunol.*, 123, 1068 (1979) and R. E. Faith et al., *NIDA Res. Monogr.*, 54, 300 (1984). Enkephalins also can enhance murine host resistance to viral and tumor challenge and to anaphylactic shock as reported by R. E. Faith et al., *Ann. N.Y. Acad. Sci.*, 496, 137 (1987). In other studies, the effects of enkephalins on immune function have been reported to be biphasic, with higher concentrations being suppressive and lower concentrations stimulatory. For example, see D. Maric et al., *Ann. N.Y. Acad. Sci.*, 496, 126 (1987) and D. R. Oleson et al., *Brain, Behavior and Immun.*, 2, 171 (1988).

Experiments to date that have examined the type of receptor on immune cells through which enkephalins exert such modulatory actions have suggested that it is an opioid receptor, similar to those found in the brain. In particular, it has been postulated that the enkephalin-binding receptor on cells of the immune system is of the delta subclass of opioid receptors. Thus, many of the effects of enkephalins on immune function can be blocked not only by the classical opioid receptor antagonist, naloxone, but also by the delta receptor-specific antagonist, ICI 174864. See, B. D. Jankovic et al., *Ann. N.Y. Acad. Sci.*, 540, 691 (1988) and R. Cotton et al., *Eur. J. Pharmacol.*, 97, 331 (1984).

NTI itself has been shown to be immunosuppressive and non-toxic both in vivo and in vitro. For example, K. Arakawa et al., in *Transplant*, 53, 951 (1992) and *Transpl. Prog.*, 24, 696 (1992) have reported using NTI to prolong allograft survival in a rat renal transplant model and to suppress in vitro allogeneic and xenogeneic mixed lymphocyte responses. In both in vitro responses, NTI was found to be less effective than cyclosporine A (CsA), the current treatment of choice for allograft survival.

The autologous mixed lymphocyte response (AMLR) is the in vitro phenomenon of T cell proliferation in response to autologous class II (Ia/DR) antigen-bearing cells (B cells, macrophages, dendritic cells or activated T cells), and thus represents a type of autoimmune reaction. The AMLR was originally characterized in mice and, subsequently, was detected in humans. The cells that proliferate in the AMLR have been shown to be capable of immunomodulation by W. E. Crowe et al., *Arth. Rheum.*, 28, 537 (1985).

It is generally believed that the AMLR can provide an in vitro model for studying immunoregulatory phenomena. For example, see, M. M. Kuntz et al., *J. Exp. Med.*, 143, 1042 (1976); M. E. Weksler et al., *J. Exp. Med.*, 146, 1833 (1977) and J. S. Smolen et al., *J. Clin. Invest.*, 68, 1601 (1981). The viability of such a model is supported by the fact that the AMLR is frequently suppressed in autoimmune diseases, as well as in other diseases arising from disorders of immunoregulation, such as infectious mononucleosis, which is caused by Epstein-Barr virus. See, for example, R. L. Hirsch, *Clin. Exp. Immunol.*, 64, 107 (1986). It has been suggested by W. E. Crowe et al., *Arth. Rheum.*, 28, 537 (1985), that this association of suppressed AMLR with autoimmune disease indicates that the impaired immunoregulation manifest in the abnormal AMLR may be related to the pathogenesis of these disorders. In their studies of the use of NTI as an immunosuppressant, H. Nagase et al. (EPA 456833) reported that NTI strongly suppresses the MLR in preparations of allogeneic murine spleen cells. Therefore, a need exists for agents which can modulate the AMLR and immunoregulatory disorders associated therewith.

SUMMARY OF THE INVENTION

The present invention provides a method for treating an immunoregulatory disease that is characterized by a depressed autologous mixed lymphocyte response (AMLR) in a mammal in need of such treatment comprising administering to said mammal an effective amount of a compound of the formula I:

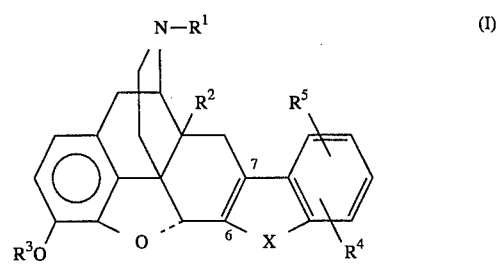

wherein $R^1$ is $(C_1-C_5)$alkyl, $C_3-C_6$(cycloalkyl)alkyl, $C_5-C_7$(cycloalkenyl)alkyl, aryl, aralkyl, trans$(C_4-C_5)$alkenyl, allyl or furan-2-ylalkyl, $R^2$ is H, OH or $O_2C(C_1-C_5)$alkyl; $R^3$ is H, $(C_1-C_5)$alkyl or $(C_1-C_5)$alkylCO; $R^4$ and $R^5$ are individually H, F, Cl, Br, NCS, $NO_2$, $NH_2$, $(C_1-C_5)$alkyl, $(C_1-C_5)$alkoxy or together are benzo; and X is O, S or NY, wherein Y is H, $(C_1-C_5)$alkyl or $(R^4)(R^5)$benzyl; and the pharmaceutically acceptable salts thereof.

A preferred compound of formula I, disclosed in U.S. Pat. No. 4,816,586, has been named "naltrindole" or "NTI" (17-(cyclopropylmethyl)-6,7-dehydro-3,14β-dihydroxy-4, 5α-epoxy-6,7-2',3'-indolmorphinan) and has the formula:

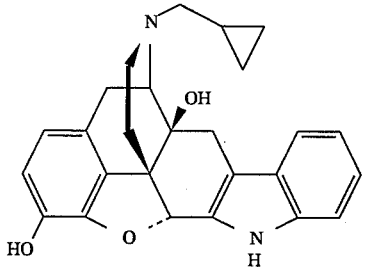
(NTI)

Another preferred compound of formula I is (17-cyclopropylmethyl)-6,7-dehydro-3,14β-dihydroxy-4,5α-epoxy-6,7-2',3'-benzo[b]furanomorphinan. See P. S. Portoghese et al., *J. Med. Chem.*, 31, 281 (1988). Another preferred compound of formula I is naltrindole 5'-isothiocyanate or "5'-NTII" (see, P. S. Portoghese et al., *J. Med. Chem.*, 33, 1547 (1990); *Eur. J. Pharmacol.*, 146, 185 (1988); *J. Med. Chem.*, 31, 281 (1988); *J. Pharmacol. Exp. Ther.*, 258, 299 (1991)). These compounds are selective δ-opioid receptor antagonists.

In another embodiment of the present method, a mammal subject to a depressed AMLR is treated with an effective amount of a compound of the formula (II):

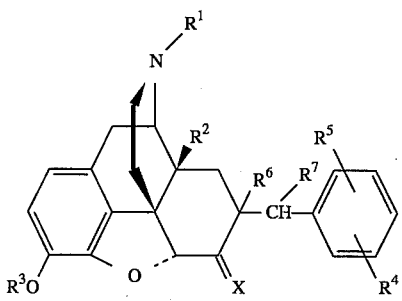
(II)

wherein $R^1$ is $(C_1-C_5)$alkyl, $C_3-C_6$(cycloalkyl)alkyl, $C_5-C_7$(cycloalkenyl)alkyl, aryl, aralkyl, trans$(C_4-C_5)$alkenyl, allyl or furan-2-ylalkyl, $R_2$ is H, OH or $O_2C(C_1-C_5)$ alkyl; $R^3$ is H, $(C_1-C_5)$alkyl or $(C_1-C_5)$alkylCO; and $R^4$ and $R^5$ are individually H, F, Cl, Br, $NO_2$, $NH_2$, NCS, $(C_1-C_5)$alkyl, $(C_1-C_5)$alkoxy or together are dioxymethylene (—OCH$_2$O—) or benzo; X is O, (H)$_2$ or CH$_2$; and $R^6$ and $R^7$ are both H or together are a bond; and the pharmaceutically acceptable salts thereof. A preferred compound of formula II is 7-benzylidenenaltrexone or "BNTX," wherein $R^1$ is cyclopropylmethyl, $R^2$ is OH, and $R^3=R^4=R^5=H$, and $R^6$ and $R^7$ together are a bond. The 6-keto (C=O) group may be absent (replaced by —CH$_2$—) or may be replaced by exo-methylene.

The present invention also provides a method of treating a depressed mammalian AMLR by administering to a human in need of such treatment, an effective amount of a biologically active compound of formula III:

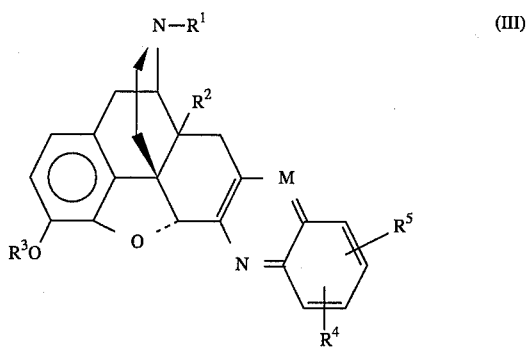
(III)

wherein $R^1$ is $(C_1-C_5)$alkyl, $C_3-C_6$(cycloalkyl)alkyl, $C_5-C_7$(cycloalkenyl)alkyl, aryl, aralkyl, trans$(C_4-C_5)$alkenyl, allyl or furan-2-ylalkyl, $R_2$ is H, OH or $O_2C(C_1-C_5)$alkyl; $R^3$ is H, $(C_1-C_5)$alkyl or $((C_1-C_5)$alkyl)C=O; M is N or CH, and $R^4$ and $R^5$ are as described for formula I hereinabove; and the pharmaceutically acceptable salts thereof.

The compounds of formulas I, II and III are selective for the δ opioid receptor. Particularly, the compounds of formula II are specific for the δ$_1$ subset of delta receptors. The delta selectivity of compounds of formulas I, II or III is apparently the salient characteristic of these compounds that allows them to elevate the depressed AMLR in the mammal, such as a human patient, to which the compound is administered. As used herein, the term "elevate" encompasses 100% elevation of the depressed response to a normal level, as well as amounts of elevation which are clinically significant to treat at least one of the associated immunoregulatory disease states, i.e., to mimic a remission. Likewise, the depressed AMLRs selected for treatment are those which are manifested by, or are symptomatic of, an acute or impending AMLR-associated disease states. Thus, the present method is effective to treat depressed AMLR-associated immunoregulatory diseases, such as autoimmune diseases, lymphoproliferative diseases and certain viral infections, both in animals and in humans.

Since the compounds of the invention are formally morphinan derivatives, it is believed that their stability and ability to cross the "blood-brain barrier" and to affect the CNS should be far superior to peptide delta opioid antagonists.

As exemplified hereinbelow, certain of the compounds of formulas I-III can also be used as intermediates in the formation of other compounds of the same class. For example, nitro groups can be reduced to amino groups.

The alkyl moiety present in the $R^1$ group which links the cycloalkyl, cycloalkenyl, aryl, or furan-2-yl moiety to the basic nitrogen atom in the compounds of formulas I, II or III is a lower(alkyl) group, preferably—(CH$_2$)$_n$—, wherein n is about 1–5, most preferably n is 1, e.g., $R^1$ is $C_3-C_6$(cycloalkyl)methyl, $C_5-C_7$(cycloalkenyl)methyl, arylmethyl or furan-2-ylmethyl. Preferred aryl moieties include $(C_6-C_{10})$aryl, preferably, $(C_6-C_9)$aryl, i.e., phenyl, benzyl, tolyl, xylyl, anisyl and the like.

The term $(R^4)(R^5)$benzyl indicates $(R^4)(R^5)$phenylmethyl, wherein $R^4$ and $R^5$ can occupy any position on the phenyl ring.

In formulas I, II or III, the position of the —$R^4$ and —$R^5$ groups indicate that they can be either ortho, meta, or para to the —X group or the —N= group, respectively, e.g., $R^4$ and/or $R^5$ can occupy any available site on the phenyl ring. In structure I, II and III, a bond designated by a wedged or darkened line indicates one extending above the plane of the phenyl rings. A bond designated by a broken line indicates one extending below the plane of the phenyl rings.

These delta-opioid antagonists include compounds of the formula I, formula II or formula III, wherein $R^1$ is ($C_1$–$C_5$)alkyl, $C_3$–$C_6$(cycloalkyl)alkyl or $C_5$–$C_7$(cycloalkenyl)alkyl, preferably wherein $R^1$ is ($C_2$–$C_3$)alkyl or $C_3$–$C_6$(cycloalkyl)methyl, and most preferably, wherein $R^1$ is cyclopropylmethyl. $R^2$ is preferably OH or OAc ($O_2CCH_3$), and $R^3$ preferably is H. Preferably, at least one, and most preferably, both of $R^4$ and $R^5$ are H, or $R^4$ is H and $R^5$ is NCS, i.e., 5'-NCS. Preferred compounds also result when $R^4$ is H and $R^5$ is F, ($C_1$–$C_5$)alkyl or ($C_1$–$C_5$)alkoxy. Preferably Y is H, methyl or benzyl. X is preferably O.

A further aspect of the present invention comprises an article of manufacture or kit comprising packaging material, such as a carton, envelope, bottle, vial, blister pack, intravenous bag and the like, and at least one pharmaceutical unit dosage form, such as a tablet or capsule, comprising an amount of a compound of formula I, II, III or a mixture thereof, effective to treat a human or animal immunoregulatory disease associated with a depressed AMLR; and wherein said packaging material comprises instruction means therein or thereon, such as a printed label, package insert, tag, cassette tape, videotape and the like, which indicates that said unit dosage form can be used to treat (elevate) a depressed human or animal AMLR, or to treat an immunoregulatory disease associated with a depressed AMLR.

DETAILED DESCRIPTION OF THE INVENTION

Depressed AMLR-Associated Diseases

Figure 1:
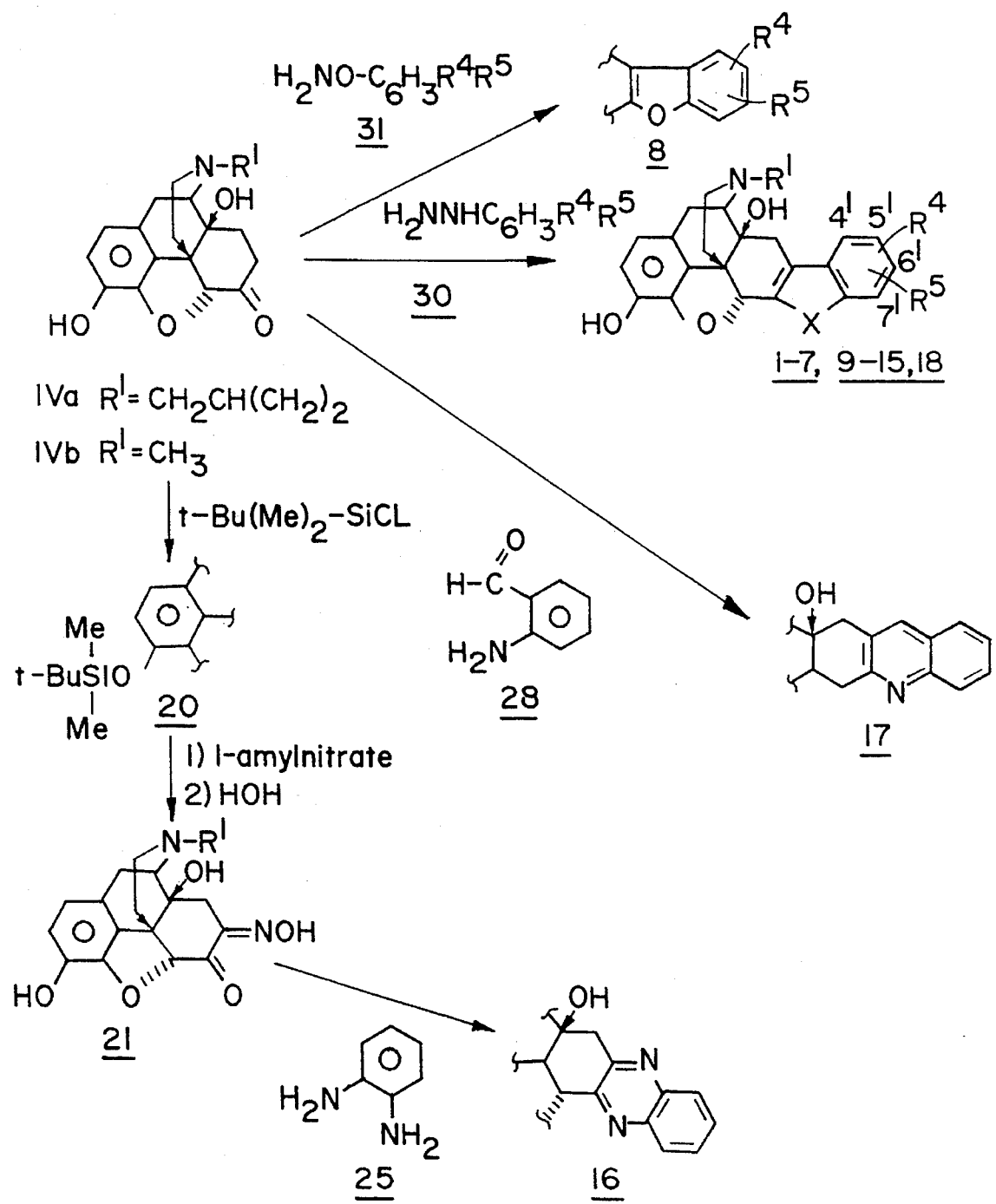
FIG. 1 is a schematic depiction of the compounds of formula I.
Figure 2A:
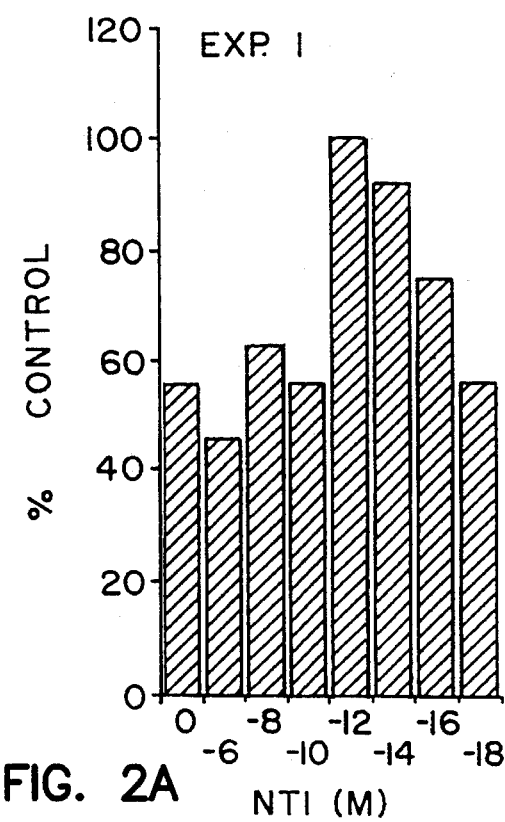
FIG. 2 contains data from six representative experiments (EXP. 1–6) which show a depressed AMLR (using rat splenic MNC) that is reversed by the addition of NTI to the cell cultures. Each experiment contains spleen cells from a pool of 3 rats. Controls were calculated from a pool of 18 uninfected rats (6 experiments).
Figure 2B:
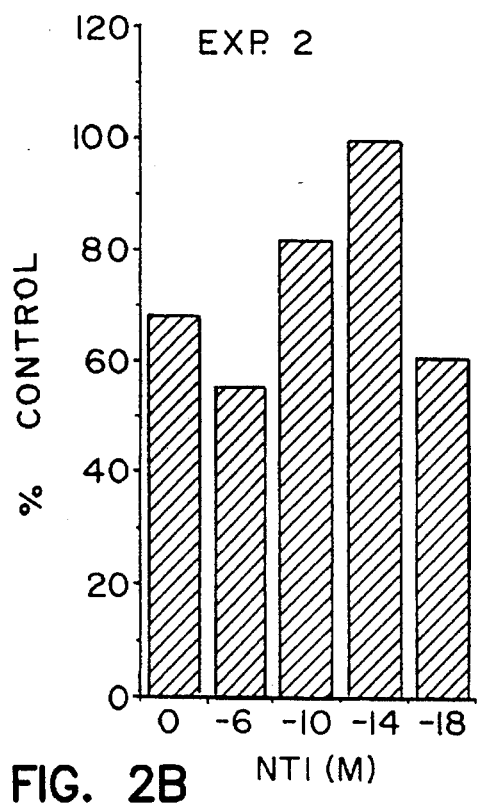
Figure 2C:
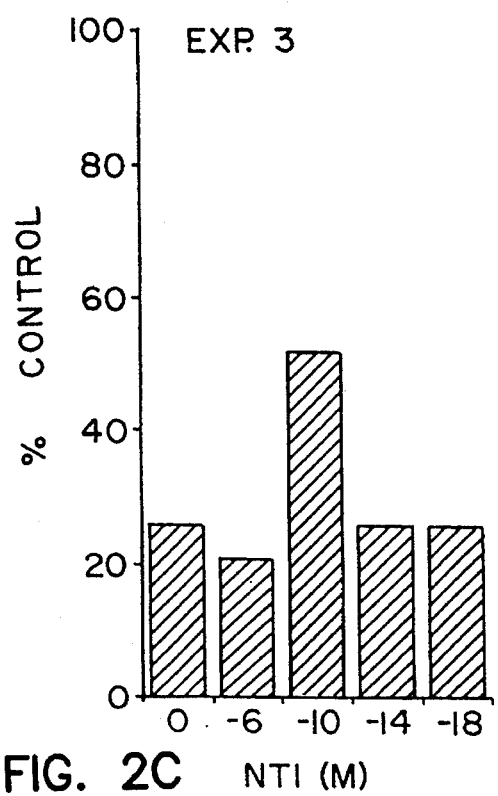
Figure 2D:
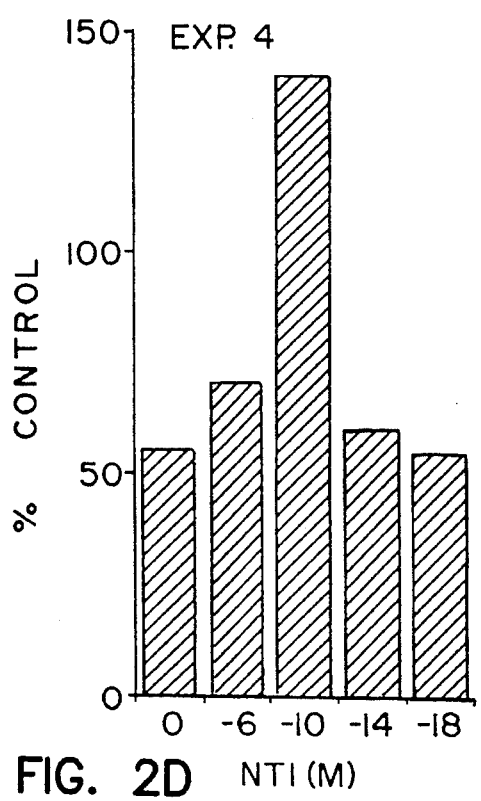
Figure 2E:
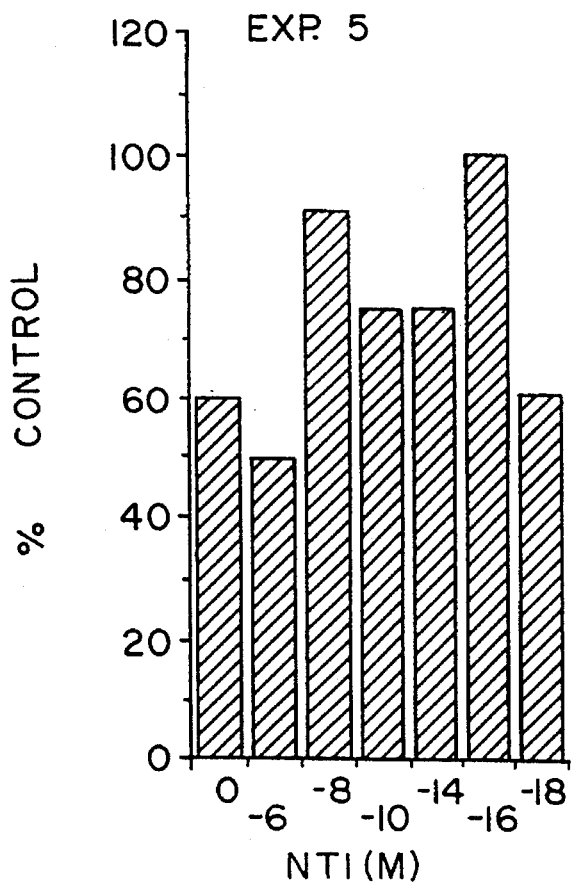
Figure 2F:
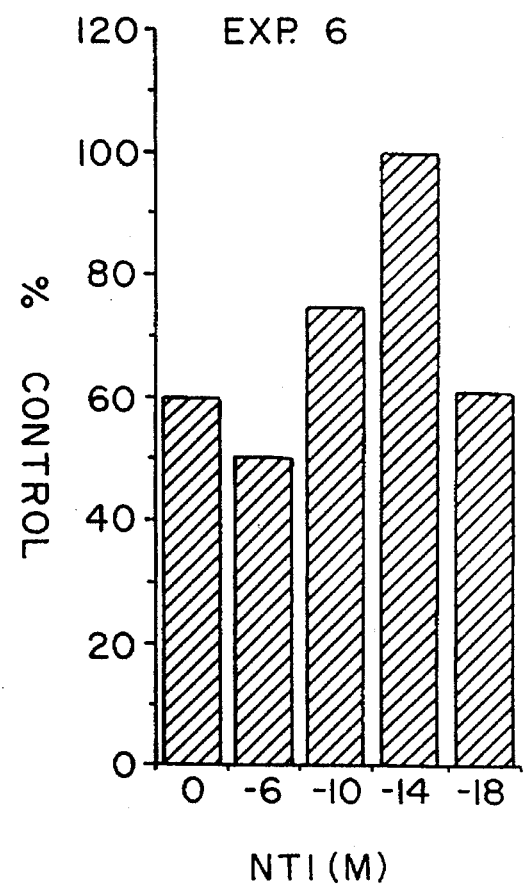

Diseases which can be treated using the present method are those characterized as disorders of immunoregulation, and include, but are not limited to, (i) autoimmune diseases, such as multiple sclerosis (MS), systemic lupus erythematosis (SLE) and rheumatoid arthritis (RA), (ii) some viral infections, including those caused by Epstein-Barr virus (EBV), cytomegalovirus (CMV), human immunodeficiency virus (HIV), Type 1 Diabetes, Newcastle Disease Virus (NDV), and lymphoproliferative disorders, such as chronic lymphocytic leukemia (CLL). Literature references describing these disease states and their association with a depressed AMLR are listed in Table A, below.

TABLE A

| Condition | Immunoregulatory Diseases Associated with AMLR Depression | |
|---|---|
| | Literature Citation |
| RA | R.L. Hirsch, Clin. Exp. Immunol., 64, 107 (1986); A. Laffor et al., Rheumatol. Int., 3, 117 (1983); S. Gupta et al., Vox Sang., 44, 265 (1983); D.A. Hafler et al., Clin. Immunol. and Immunopathol., 58, 115 (1991). |
| EBV | S. Gupta et al., Vox Sang., 44, 265 (1983). |
| Type 1 Diabetes | S. Gupta et al., Vox Sang., 44, 265 (1983). |
| CMV | Cytomegalovirus - Biology and Infection, M. Ho, ed., Plenum, NY (1982) at pages 223–243. |
| HIV | F. Puppo et al., AIDS Res. Hum. Retroviruses, 3, 423 (1987); E.C. Ebert et al., Clin. Immunol. Immunopathol., 37, 283 (1985). |
| CLL | T. Han et al., Blood, 60, 1075 (1982). |
| Sjogren's Syndrome | D.A. Haffer et al., Immunol. Today, 10, 104 (1989). |

As discussed hereinabove, and by J. K. Gutowski et al., Immunol., 46, 801 (1982), the AMLR is a measure of the capacity of T lymphocytes to proliferate in response to autoantigens and is thought to be indicative of T cell regulatory ability. The suppressor-inducer subset of CD4 T cells (CD4+ 45R+) appears to be the primary cell activated by the autoantigens presented by the antigen presenting cells in the cultures. The primary functional consequence of the activation of these cells in the AMLR has been shown to be the generation of suppressor T cells, which is manifested by the magnitude of proliferation in the AMLR assay. See D. Kelleher et al., Gut, 30, 839 (1989); D. A. Hafler et al., Clin. Immunol. and Immunopathol., 58, 115 (1991); J. K. Gutowski et al., Immunol., 46., 801 (1982); F. Pazderka et al., Cell. Immunol., 112, 64 (1988).

As discussed by J. K. Gutowski et al., Immunol., 46, 801 (1982), humans and animals with autoimmune diseases associated with suppressor cell dysfunction show impaired AMLR activity. It is believed that the absence of AMLR-generated suppressor cells, or suppressor cell function, may be pathogenetically related to the loss of self-tolerance in these individuals. Agents that can reverse a depressed AMLR can be effective for the treatment of diseases which are characterized by a depressed AMLR, since it has been demonstrated by A. Laffer et al., Rheumatol. Int., 3, 117 (1983), that the AMLR returns to normal levels in patients with autoimmune diseases which are in remission, either due to treatment or as a natural part of the disease process. Thus, the reversal of the depressed AMLR by the present compounds may be due to enhanced suppressor cell activity, which in turn can mimic the normal remission of autoimmune diseases.

The depressed AMLR elevated as taught hereinbelow, was a consequence of both an uncontrolled viral infection in a rat colony and a controlled infection of mice with murine cytomegalovirus (mCMV). Since the mechanisms involved in all of these immunoregulatory disorders are complex, it may be questioned as to whether the correction of an in vitro defect relating to two diseases can be related in general to all diseases of this type. However, there is strong evidence to suggest that it is. Patients with HIV infection have been shown to have a depressed AMLR which is related, in part, to a lack of IL-2 production and IL-2 receptor (IL-2R) expression, both of which are necessary for T cells to function. These same functional defects (i.e., depressed AMLR, depressed IL-2 production and IL-2R expression) have been described in mice infected with New Castle Disease virus (NDV) and in all strains of mice which are susceptible to autoimmune diseases, suggesting that common mechanisms are defective in different immunoregulatory disorders. See N. Tala et al., *Behring Inst. Mitt.*, 72, 169 (1983). Thus, the ability of NTI to reverse the depressed AMLR which occurs in rats and mice following a viral infection can be generalized to all diseases involving disorders of immunoregulation, particularly in view of its stability and its ability to cross the blood/brain barrier.

Chemistry

Representative compounds of formula I (1–15 and 18) or formula III (16–17) were synthesized from starting materials of formula IVa or IVb as outlined in FIG. 1, as described in U.S. Pat. No. 4,816,586. The structures of compounds 1–15 and 18, shown generally in FIG. 1, are summarized on Table I, below.

TABLE I*

| Compound No. of Table I | $R^1$ | X | $R^4$ | $R^5$ |
|---|---|---|---|---|
| 1 | CpCH$_2$[1] | NH | H | H |
| 2 | CpCH$_2$ | NCH$_3$[2] | H | H |
| 3 | CpCH$_2$ | NH | H | 5'-F |
| 4 | CpCH$_2$ | NH | H | 5'-OCH$_3$ |
| 5 | CpCH$_2$ | NH | H | 5'-CH$_3$ |
| 6 | CpCH$_2$ | NH | H | 5'-NO$_2$ |
| 7 | CH$_3$ | NH | H | H |
| 8 | CpCH$_2$ | O | H | H |
| 9[3] | CpCH$_2$ | NH | H | 5'-OH |
| 10 | CpCH$_2$ | NH | H | 4'-F |
| 11 | CpCH$_2$ | NH | H | 7'-F |
| 12 | CpCH$_2$ | NH | H | 4' and 6'-CH$_3$ (Mixture) |
| 12a | CpCH$_2$ | NH | H | 5'-NH$_2$ |
| 12b | CpCH$_2$ | NH | H | 5'-NCS |
| 13 | CpCH$_2$ | NH | H | 7'-CH$_3$ |
| 14 | CpCH$_2$ | NH | H | 7'-OCH$_3$ |
| 15[4] | CpCH$_2$ | NH | H | 7'-OH |
| 18 | CpCH$_2$ | NH | 6'-CH=CH—CH=CH-7' | |

[1]Cyclopropylmethyl.
[2]From Fischer indole synthesis of IVa + H$_2$NN(CH$_3$)Ph.
[3]Derived from 4 using five equivalents of BBr$_3$.
[4]Hydrolysis product formed during synthesis of 14.
*From Portoghese et al. (U.S. Pat. No. 4,816,586).

Compounds 1–18 have either indole (1–7, 9–15), benzofuran (8), benzopyrazine (16), benzoquinoline (17) or benzoindole (18) moieties, fused to the 6,7-position of the opiate C-ring.

Starting Materials

The structures, common names and Merck Index reference numbers of representative 4,5-epoxy-6-keto-morphinan starting materials of general formula IV are summarized on Table II, below.

TABLE II*

| Compound | $R^1$ | $R^2$ | $R^3$ | Common Name | Merck No.[2] |
|---|---|---|---|---|---|
| IVa | CH$_2$CH(CH$_2$)$_2$ | OH | H | naltrexone | 6209 |
| IVb | CH$_3$ | OH | H | oxymorphone | 6837 |
| IVc | CH$_3$ | H | H | hydromorphone | 4714 |
| IVd | CH$_3$ | H | CH$_3$ | hydrocodone | 4687 |
| IVe[1] | CH$_2$CH(CH$_2$)$_2$ | H | H | — | — |
| IVf | CH$_2$CH=CH$_2$ | OH | H | naloxone | 6208 |
| IVg | CH$_3$ | OH | CH$_3$ | oxycodone | 6827 |

[1]Preparation, M. Gates et al., J.Med.Chem., 7, 127 (1964).
[2]The Merck Index, W. Windholz, ed., Merck & Co., Rahway, NJ (10th ed. 1983).
*Portoghese et al. (U.S. Pat. No. 4,816,586).

Other starting materials of formula IV can be prepared by synthetic methods which are well known in the art of organic chemistry. For example, compounds of formula IV wherein $R^1$ is H and $R^3$ is a suitable protecting group, and wherein the 6-keto group has also been protected, can be prepared from compounds IVa–g. These intermediates can be N-alkylated and deprotected to yield compounds of formula I wherein $R^1$ is $C_2$–$C_5$(alkyl), $C_4$–$C_6$(cycloalkyl)alkyl, $C_5$–$C_7$(cycloalkenyl)alkyl, aryl, aralkyl, trans-$C_4$–$C_5$-alkenyl or furan-2-ylalkyl, by the application of well known reactions.

For example, the free hydroxyl groups of compounds of formula IV, e.g., $R^2$=OH and/or $R^3$=H, can be protected by acid-labile groups such as tetrahydropyranl-yl, trimethylsilyl, 1-methoxy-isopropyl and the like as disclosed in *Compendium of Organic Synthetic Methods*, I. T. Harrison et al., eds., Wiley-Interscience, New York, N.Y. (1971) at pages 124–131, (hereinafter "Compendium"), the disclosure of which is incorporated by reference herein. The protection of the 6-keto group of compounds of formula IV by its reversible conversion into a ketal or a thioketal group is disclosed in Compendium, at pages 449–453, the disclosure of which is incorporated by reference herein. Methods for the demethylation of N-methyl amines have been disclosed, for example, in Compendium at page 247, *J. Amer. Chem. Soc.*, 89, 1942 (1967) and *J. Amer. Chem. Soc.*, 77, 4079 (1955), the disclosures of which are incorporated by reference herein.

Procedures for the alkylation of secondary amines with halides under basic or neutral conditions are well known. For example, see Compendium at pages 242–245; *Org. Synth.*, 43, 45 (1963); *J. Org. Chem.*, 27, 3639 (1962) and *J. Amer. Chem. Soc.*, 82, 6163 (1960), the disclosures of which are incorporated by reference herein.

Synthesis of Delta Opioid Receptor Antagonists

Compounds of formulas I, II or III wherein $R^2$ is acyloxy and/or $R^3$ is acyl can be prepared by using the corresponding starting material IV. For example, starting material IVa can be diacylated by reacting it with the appropriate ($C_1$–$C_5$)alkyl anhydride in pyridine for 10–18 hrs at 18°–25° C. The resultant 3,14-diacylated compound can be converted to the 14-acylated compound by limited hydrolysis. The 3-acylated starting materials can be prepared by the short-term reaction of the compound of formula IV with the anhydride, e.g., for about 2–4 hours. The 3-acylated product can be separated from the 3,14-diacylated product by chromatography.

Compounds of formula II wherein X is exo-methylene can be prepared by reacting the 6-keto group with $CH_2=PPh_3$. Compounds of formula II wherein X is $(H)_2$ can be prepared by hydrogenolysing the corresponding thioketal or dithianyl-protected 6-keto group.

The preparation of 1–7, 9–15 and 18 was accomplished using the Fischer indole synthesis. See R. B. Van Orden et al., *Chem. Rev.*, 30, 78 (1942), the disclosure of which is incorporated by reference herein. A compound of formula IV, e.g., naltrexone hydrochloride (IVa.HCl) or oxymorphone hydrochloride (IVb.HCl) and the appropriate aromatic hydrazine hydrochloride (30) were refluxed in glacial acetic acid or methanol containing an organic or inorganic acid such as methanesulfonic acid or hydrochloric acid (HCl) for 3–6 hours. Compound 12b was prepared by reducing 5'-nitroindole (6) to the 5'-amino derivative 12a, which was treated with thiophosgene to yield 12b, as the hydrated salt. See P. S. Portoghese et al., *J. Med. Chem.*, 31, 281 (1988). The 6',7'-benzo-derivative (18), was prepared by refluxing naltrexone.HCl with 1-napthylhydrazine.

Benzofuran 8 was prepared by refluxing an ethanol solution containing equivalent amounts of IVa.HCl, methane sulfonic acid and o-phenylhydroxylamine.HCl (31) for 18 hours.

The benzopyrazine 16 was synthesized from IVa.HCl by a conversion to the oximino derivative 21 followed by reaction with o-phenylenediamine 25.

The quinoline derivative 17 was prepared by refluxing naltrexone.HCl with o-aminobenzaldehyde 28 and methanesulfonic acid in ethanol. The corresponding benzothiophene derivatives (I, X=S) can be synthesized by reacting a compound of formula IV with thiophenol in the presence of an acid, followed by photolysis of the OH-protected thioenol under a nitrogen atmosphere using a Hg high pressure lamp (see S. H. Green et al., *J. Org. Chem.*, 33, 2218 (1968), the disclosure of which is incorporated by reference herein).

The acid salts of compounds of formulas I, II, or III, wherein $R^3$=H can be converted into the corresponding ($C_1$–$C_5$)alkoxy derivatives [$R^3$=($C_1$–$C_5$)alkyl] by dissolving the starting material in DMF and adding an excess of the appropriate ($C_1$–$C_5$)alkyl iodide and an amine such as diisopropylethylamine. The reaction can be conducted at an elevated temperature for about 4–10 hours. The final product can be purified by column chromatography.

Pharmaceutically acceptable amine salts of these compounds may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. These physiologically acceptable salts are prepared by methods known in the art, e.g., by dissolving the free amine bases with an excess of the acid in aqueous alcohol.

The synthesis of compounds 1–12 and 13–17 is set forth in detail in P. S. Portoghese (U.S. Pat. No. 4,816,586), the disclosure of which is incorporated by reference herein.

The compounds of formula II can be readily synthesized by reacting a compound of formula IV with benzaldehyde or a mono- or di-substituted derivative thereof in the presence of base, as shown below.

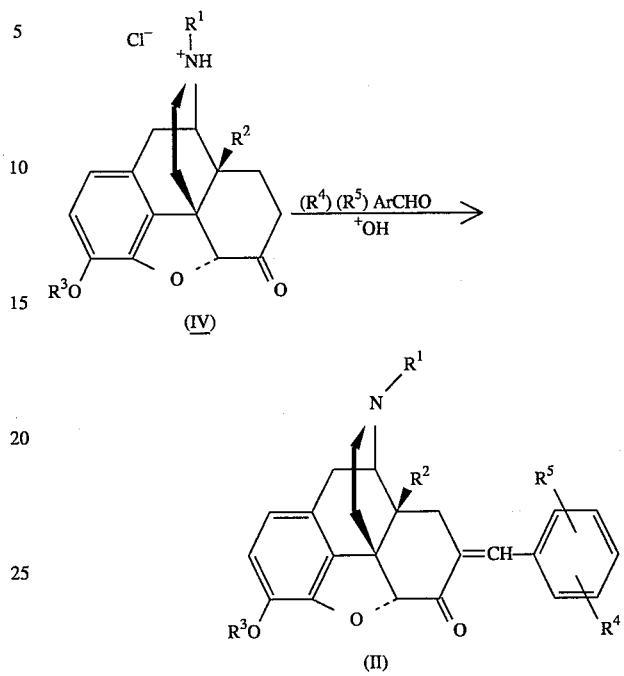

wherein $R^1$, $R^2$, $R^3$, $R^4$ and $R^5$ are as disclosed hereinabove. Preferably, IV is naltrexone hydrochloride, e.g., $R^3$=H, $R^2$=OH and $R^1$ is cyclopropylmethyl, and the synthesis of compound II wherein $R^2$OH, $R^1$=cyclopropylmethyl and $R^3$=$R^4$=$R^5$=H is carried out as described by P. S. Portoghese et al., *J. Med. Chem.*, 34, 1292 (1991). When $OR^3$ and/or $R^2$ are base-liable groups such as alkanoxy, $R^3$ may be H and $R^2$ may be OH in the compound of formula II. In such situations, the protecting groups can be replaced by art-recognized methodologies for the protection/deprotection of hydroxyl groups. Of course, if naltrexone.HCl or a similar compound of formula IV, comprising free OH groups is used to prepare compounds of formula II wherein $R^3$ is H and/or $R^2$ is OH or H, the free hydroxyl groups in the compound of formula II can be also converted to alkanoyloxy groups by methods known to the art.

The synthesis of specific embodiments of the compounds of formula II is set forth in detail in U.S. patent application Ser. No. 07/867,997, filed Apr. 13, 1992.

Administration and Dosage Forms

In the clinical practice of the present method, the compounds of the present invention will normally be administered orally or parenterally, as by injection or infusion, in the form of a pharmaceutical preparation comprising the active ingredient in combination with a pharmaceutically acceptable carrier, e.g., in the form of a pharmaceutical unit dosage form. The carrier may be a solid, semi-solid or liquid diluent or be compressed or shaped into an ingestible capsule. The compound or its salt may also be used without carrier material.

Examples of pharmaceutical unit dosage forms comprising the present antagonists include tablets, pre-selected volumes of intravenous solutions, suspensions, hard or soft gelatin capsules, microcapsules, suppositories, liposomes and systems designed for controlled or prolonged release of the active agent, such as reservoirs designed for transdermal delivery or subcutaneous delivery. Such reservoirs include skin patches and shaped polymeric implants. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

Doses of a given compound of formulas I, II or III which are effective to counteract a depressed AMLR, and to treat the symptomology of the resultant disease state can be extrapolated, to some extent, from the in vitro murine data disclosed hereinbelow and from the in vivo murine data presented in Eur. J. Pharmacol., 219, 346 (1992) and J. C. Froehlich et al., Alcoholism, 15, 315, abstract 20 (1991), by methods known to the art for extrapolation of animal dosing data to humans. For example, see U.S. Pat. Nos. 5,035,878 and 4,938,949.

Bioassays

A. Tests Using Guinea Pig Ileal Muscle

When the extracted longitudinal muscle from the guinea pig ileum (GPI) is suspended in a physiological medium, electrical stimulation reliably produces contractions. Responsiveness to the electrical stimulation, therefore, can be used to index the effects of drugs. The procedures used and common results have become standard, as exemplified by the observations that morphine reliably suppresses the contractions that would ordinarily follow from the electrical stimulation and classic opioid antagonists, such as naloxone and naltrexone, block morphine's effects.

B. Mouse Vas Deferens (MVD)

The mouse vas deferens is sensitive to deltaopioid drugs. Furthermore, the MVD responds selectively to delta opioids. It is, therefore, useful in indexing selective delta-opioid drugs. The methods used here are described by Henderson et al. (Brit. J. Pharmacol., 46, 764 (1972)), the disclosure of which is incorporated by reference herein.

EXAMPLE 1

EVALUATION OF ANTAGONIST ACTIVITY

A. Materials and Methods

1. Guinea Pig Ileal Longitudinal Muscle (GPI). Ileal from guinea pigs were taken approximately 10 cm from the ileocaecal junction, and a strip of longitudinal muscle with the myenteric plexus attached was prepared by method of Rang et al., Brit. J. Pharmacol., 22, 356 (1964), the disclosure of which is incorporated by reference herein. A 1 cm portion of this strip was then mounted between two platinum electrodes placed in a 10 ml organ bath and connected to an isometric transducer. Contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 µM chlorpheniramine maleate was the bathing solution and was continuously bubbled with 95% $O_2$ and 5% $CO_2$. The organ bath was maintained at 36°–37° C. The longitudinal muscle strip was allowed to equilibrate with continuous stimulation for a minimum of 90 min. Cumulative concentration-response curves were determined after drugs were added to the bath in 10- to 50-µL amounts and washed out with two 10 ml portions of buffer after noting their maximum effects.

2. Mouse Vas Deferens (MVD). This assay was performed according to the description by Henderson et al., Brit. J. Pharmacol., 46, 764 (1972), the disclosure of which is incorporated by reference herein. Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10- to 50-µL amounts and washed out after noting their maximum effect.

B. Pharmacology

The compounds were tested in vitro on the mouse vas deferens (MVD) and guinea pig ileum (GPI) preparations. Each compound (100 or 200 nM) was incubated for 15 min with the tissue prior to adding graded doses of a standard agonist for determination of an $IC_{50}$ value. The standard agonists employed were [D-Ala$^2$, D-Leu$^5$]enkephalin (DADLE), morphine (M), and ethylketazocine (EK); these are selective for delta, mu, and kappa opioid receptors, respectively. The $IC_{50}$ value was divided by the control $IC_{50}$ value in the same tissue, and this $IC_{50}$ ratio (DR) was employed to calculate the Ke value using the equation Ke=[antagonist]/(DR-1). The results of these bioassays are summarized on Table III, below.

TABLE III*

In Vitro Antagonist Activity of 6,7-Dehydro-3,14-dihydroxy-4,5α-epoxymorphinan Derivatives

| Compound No. | Ke (nM)[a] | | |
|---|---|---|---|
| | DADLE[b] | M[c] | EK[d] |
| 1 | 0.22 | 29.4 | 45.5 |
| 2 | 1.5 | 12.5 | 22.2 |
| 3 | 2.0 | 61.7 | 46.2 |
| 4 | 5.7 | 63.0 | 12.6 |
| 5 | 4.2 | >160 | >250 |
| 6 | 168.0 | 92.0 | ≧200 |
| 7 | e | e | e |
| 8 | 1.8 | 30.8 | 50.8 |
| 9 | — | 27.2 | 68.5 |
| 10 | 5.5 | >125 | >170 |
| 11 | 0.35 | 5.3 | >330 |
| 12 | 4.8 | >125 | >143 |
| 13 | 1.5 | 19.1 | >330 |
| 14 | 6.6 | 35 | — |
| 16 | 1.4 | 6.1 | 13.4 |
| 17 | 2.7 | 11.3 | 16.3 |

[a]Ke = [antagonist]/($IC_{50}$ ratio − 1), where the $IC_{50}$ ratio represents the response of the tissue to an agonist in the presence of the antagonist divided by the control $IC_{50}$ of the agonist in the same tissue.
[b][D-Ala$^2$, D-Leu$^5$]enkephalin in the mouse vas deferens preparation (MVD).
[c]Morphine in the guinea pig ileum preparation (GPI).
[d]Ethylketazocine in the GPI.
[e]No agonist antagonism observed.
*From Portoghese et al. (U.S. Pat. No. 4,816,586).

All of the N-cyclopropylmethyl compounds (1–6, 8–14 and 16–17) antagonized the effect of the delta agonist, DADLE. Substantially less antagonism toward morphine and EK was observed. These compounds were devoid of agonist activity or behaved as weak, partial agonists, with dose-response curves that plateaued at 20–40% of the maximal response at a concentration of 1 µM. The agonist effect was consistently below 20% at the concentrations employed (20–200 nM) for antagonist testing.

The N-methyl compound 7 also exhibited partial agonist activity. However, because its agonist effect was below 20% only at 5 nM or less, it was tested for antagonist activity at this concentration and was found to be inactive in this regard.

EXAMPLE 2

ANTAGONIST ACTIVITY OF NTI IN VIVO

The highly active delta antagonist NTI (1) of the series was evaluated in mice for its effectiveness in antagonizing the antinociceptive effect of Tyr-D-Ser-Gly-Phe-Leu-Thr (DSLET), morphine, and U50488H. These agonists were employed because their agonist activity is selectively mediated through delta, mu, and kappa opioid receptors, respectively.

TABLE IV*

| In Vivo Antagonist Activity of NTI (1) in Mice* | |
|---|---|
| Agonist | $ED_{50}$ Ratio[a] |
| DSLET[b] | 5.25 (2.70–11.11) |
| Morphine[c] | 1.15 (0.54–2.78) |
| U50488H[c] | 1.23 (0.63–2.86) |

*Methodology of G. Hayashi et al., Eur. J. Pharmacol., 16, 63 (1971).
[a]$ED_{50}$ value of treated mice (20 mg/kg s.c.) divided by $ED_{50}$ of control mice.
[b]Administered intracerebroventicularly (i.c.v.).
[c]Administered subcutaneously (s.c.).
*From Portoghese et al. (U.S. Pat. No. 4,816,586).

As shown by the data on Table IV, compound 1 at 20 mg/kg s.c. effectively blocked the writhing inhibition due to DSLET ($ED_{50}$ ratio=5) without significantly antagonizing the effect of morphine or U50488H.

Therefore, both the in vitro and in vivo data show that fusion of the indole, benzofuran, benzopyrazine or quinoline ring system to the C-ring of naltrexone gives rise to compounds that possess a unique opioid receptor antagonist profile. Most of these compounds are highly selective for the delta opioid receptor, and the unsubstituted indole 1 appears to be an order of magnitude more potent than its substituted congeners. The selectivity ratios of NTI are approximately 50 for delta/mu, and possibly greater for delta/kappa.

It can be noted that the benzofuran 8, while less potent and less selective than 1 as a delta antagonist, nevertheless retains substantial delta antagonist activity. A similar relationship was observed with the benzopyrazine 16 and the quinoline 17. This indicates that the indole ring system is not necessary for delta selectivity. Possibly, the role of the pyrrole, furan, pyrazine and quinoline moieties in these compounds is to restrain the additional benzene ring so that it is a coplanar to the C-ring of the morphinan nucleus.

Example 3

Effect of NTI on Depressed AMLR in Rat Coronavirus Infection

Rats.

Male Lewis rats, 150 g, were obtained from Harlan-Sprague Dawley, Inc. (Indianapolis, Ind.) and housed in conventional rat cages for at least one week prior to each experiment. Rats were given food and water ad libitum and maintained on a 12hr:12hr light:dark cycle.
Isolation of splenic mononuclear cells (MNC).

Rats were anesthetized with a mixture of 8 mg/ml ketamine and 2 mg/ml acepromazine (dose=0.1 ml/100 g body weight) and the spleens were removed aseptically. The animals were exsanguinated while under anesthesia. Splenic MNC were released from the surrounding connective tissue by dispersing through a wire mesh. The red blood cells were removed by density gradient centrifugation on ficol-hypaque (Lymphocyte Separation Medium, LSM, Organon Tecknika, Durham, N.C.). The purified MNC were washed in Hanks Balanced Salt Solution containing 1% gelatin and 2 mM EDTA and resuspended in RPMI-1640 medium containing 5% Fetal Bovine Serum (FBS), 100 U/ml penicillin, 100 ug/ml streptomycin and $5 \times 10^{-5}$M 2-mercaptoethanol. In some experiments, TCM™, a defined medium supplement (CELOX, Minneapolis, Min.), was used instead of FBS.
Autologous cell cultures.

Purified MNC were placed in 96-well round bottom plates at $2 \times 10^5$ cells/well in a total volume of 0.2 ml and incubated for 5 days at 37° C. To some wells, NTI (obtained from Dr. P. Portoghese, University of Minn, ref 9) at concentrations ranging from $10^{-6}$M to $10^{-18}$ mM was added at the start of culture. For the final 18 hr of culture, 1 uCi of $^3$H-thymidine (6.7 Ci/mmole, New England Nuclear, Boston, Mass.) was added to each well. The cells were then harvested onto glass fiber filter paper and counted in a Beckman (Fullerton, Calif.) scintillation counter. The results are calculated as the mean counts per minute of triplicate wells, and are expressed as percent of control (cpm suppressed AMLR/cpm control AMLR).

The most common procedure to conduct an AMLR assay is to separate the T cells from the non-T cells, irradiate or mitomycin-C treat the latter, and recombine them in culture. Such manipulations result in somewhat higher cpm in the cultures, however, and it has been shown by R. I. Zuberi et al., Cell. Immunol., 84, 299 (1984), that unfractionated splenic MNC which incorporate $^3$H-thymidine in these cultures are also doing so in response to autologous antigens. Thus, unfractionated splenic MNC cultured alone in the manner described in this example produce a true AMLR.
Rat Coronavirus infection.

Some of the rats in our colony displayed clinical signs of infection with rat coronavirus, as diagnosed by our veterinarian. This virus causes an upper respiratory infection which is not fatal, but which is known to be immunosuppressive. See R. O. Jacoby et al., in The Laboratory Rat, Vol. I, Biology and Diseases, H. J. Baker et al., eds., Academic Press, New York (1979) at page 272. The rats typically recovered within a week to ten days of becoming sick. Splenic MNC from infected rats consistently showed a depressed AMLR. Control responses were obtained from splenic MNC isolated from uninfected rats.

NTI Administration

In FIG. 1 are shown the results of six representative experiments (labeled Exp. 1–6) in which autologous mixed lymphocyte responses from infected rats (the cells harvested from 3 rats were pooled for each experiment) were modulated by NTI and measured by 3H-thymidine incorporation. The responses are expressed as percent (%) of control responses, which were obtained using MNC isolated from uninfected rats. The control counts ranged from 3800 to 5200 cpm when 5% FBS was used in the culture medium. Slightly lower counts were seen when TCM™ replaced the FBS in the medium (1200–1500 cpm). TCM™ was used in two AMLR experiments (data not shown) to demonstrate that the $^3$H-thymidine incorporation seen in control cultures was truly an AMLR and not due to mitogenic stimulation by xenogeneic serum.

In all experiments, the suppression of the AMLR in cells from infected rats compared to control cells from healthy rats was only partial, ranging from 32% (Exp. 2 is shown as 68% of control) to 75% (Exp. 3). For all 6 experiments, the percent suppression was 52±8 (mean± s.e.m.). These responses are typical of those seen in patients with multiple sclerosis, for example, in which suppressed patient AMLR are approximately 50% of those of healthy controls. For example, see R. L. Hirsch, *Clin. Exp. Immunol.*, 64, 107 (1986); D. A. Hafler et al., *Clin. Immunol. and Immunopathol.*, 58, 115 (1991).

In our experiments, the addition of NTI to the suppressed cultures exhibiting an AMLR generally resulted in complete, or almost complete, restoration of the response (normal proliferation), as measured by 3H-thymidine incorporation. The most severely suppressed responses, shown in Experiment 3, were only partially restored by the concentrations of NTI used in this experiment. It is possible, however, that $10^{-12}$M NTI would have completely reversed the suppressed responses in these cultures. Concentrations of NTI that were most effective in reversing depressed AMLR were generally in the range of $10^{-10}$M to $10^{-14}$M.

Example 4

NTI Effect on Depressed AMLR in Murine Cytomegalovirus (mCMV) Infection

Mice.

Eight-week-old male Balb/C mice were obtained from Harlan-Sprague Dawley, Inc. (Indianapolis, Ind.) and housed in conventional mouse cages for at least one week prior to each experiment. Mice were given food and water ad libitum and maintained on a 12hr:12hr light:dark cycle.

mCMV infection.

Mice were injected i.p. with serial 10-fold dilutions of a stock mCMV solution. Dilutions of stock virus ranged from $10^{-2}$ to $10^{-6}$. Mice were sacrificed after 10 days of infection. Control mice were injected with saline.

Isolation of T and non-T MNC fractions.

Splenic MNC from CMV-infected and uninfected mice were purified by density gradient centrifugation on LSM, as described above for the rat splenic MNC. T and non-T cell fractions were separated by nylon wool columns as disclosed by M. H. Julius et al., *Eur. J. Immunol.*, 3, 645 (1973). The T-enriched cells were used as responder cells. The non-T cells were treated with mitomycin-C to stop their proliferation, as described by K. M. Linner et al., *Endocrinol.*, 128, 717 (1991) and used as stimulator cells. Autologous cell cultures were then set up, with equal numbers ($2 \times 10^5$) of responder T and stimulator non-T cells being cultured in the 96-well microtiter plates. Cells were cultured for 5 days. To some wells, NTI at $10^{-10}$, or $10^{-14}$, concentrations determined to be optimal from the rat AMLR studies, was added for the duration of the culture period. $^3$H-thymidine was added to each well for the last 18 hr of incubation, and the cultures were harvested and counted as described above.

In FIG. 2 are shown the results of in vivo mCMV infection on the AMLR. At 10 days following infection with CMV, maximal suppression of the AMLR was seen with CMV at $10^{-4}$. CMV at $10^{-5}$ and $10^{-6}$ had no effect on the AMLR at this time, whereas CMV at $10^{-3}$ and $10^{-2}$ suppressed the AMLR to a lesser extent. The control (uninfected) AMLR had cpm ranging from 4500 to 14,500.

Figure 3:
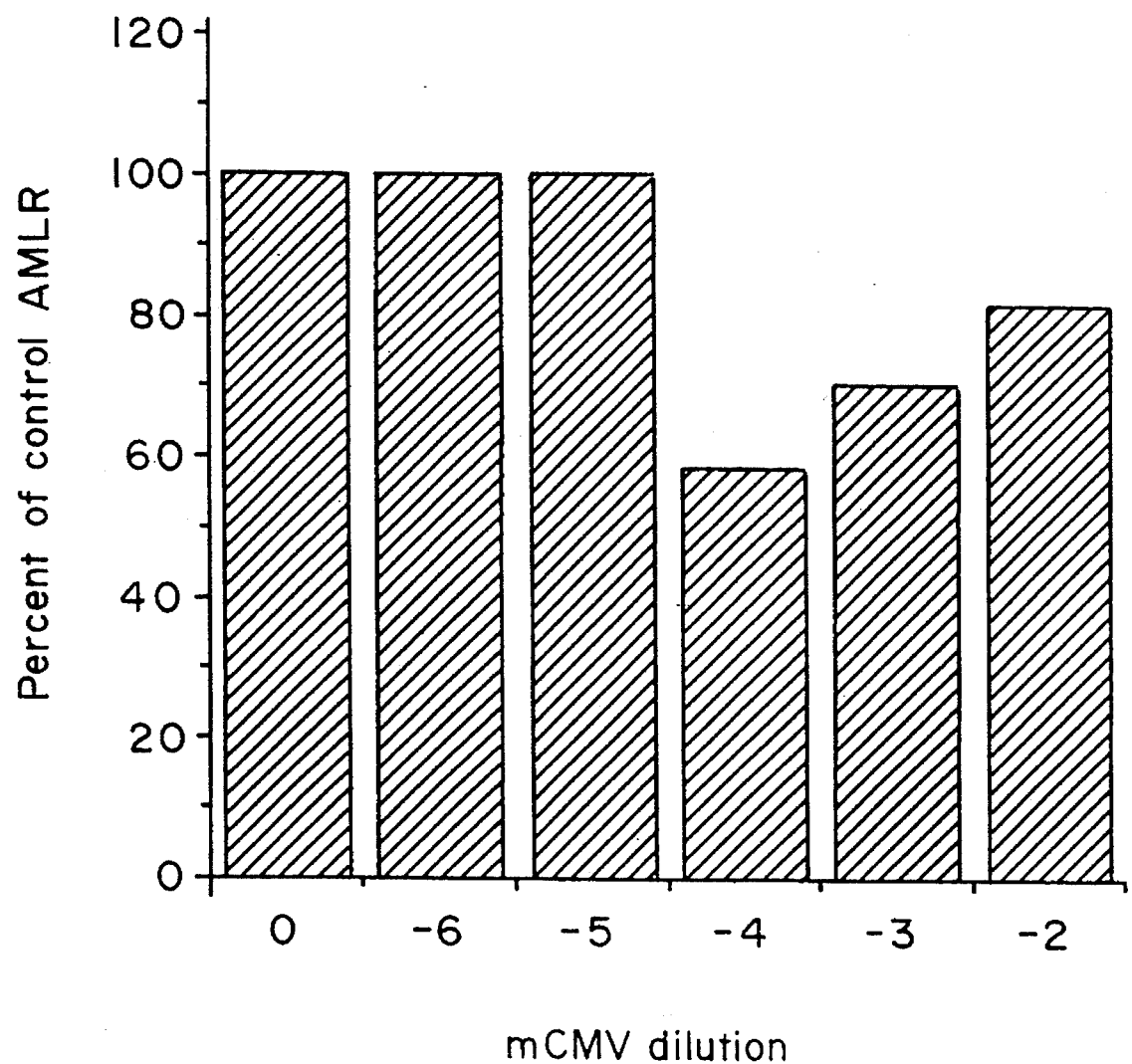
FIG. 3 shows that deliberate infection of mice with mCMV results in a suppressed AMLR that is dose-dependent. Uninfected mice were injected with saline at the same time that the infected mice received mCMV. Each treatment group consisted of cells pooled from two mice.
Figure 4A:
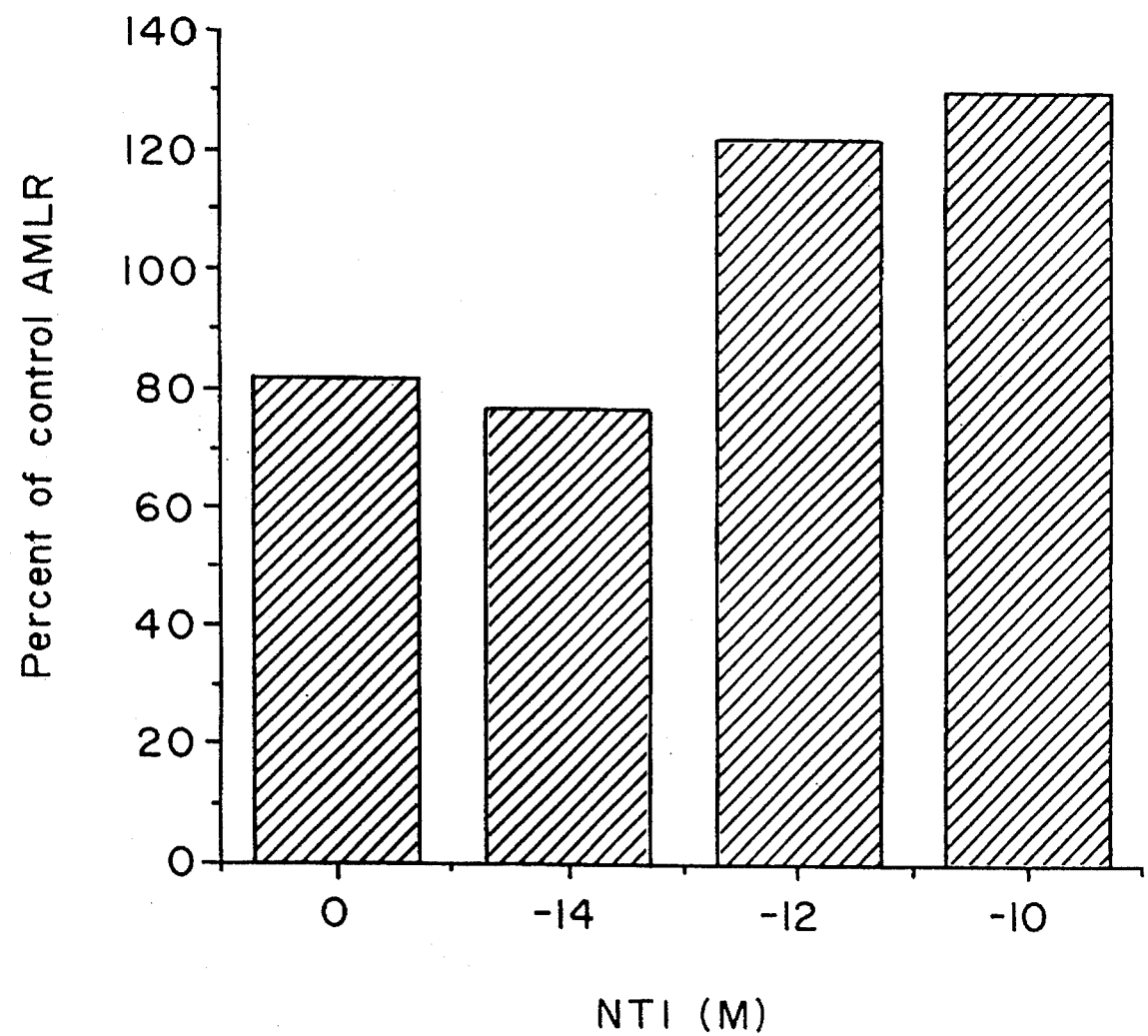
FIGS. 4A and 4B show that NTI can reverse the suppressed AMLR caused by CMV infection. Optimal concentrations of NTI were determined from the rat AMLR experiments shown in FIG. 1.
Figure 4B:
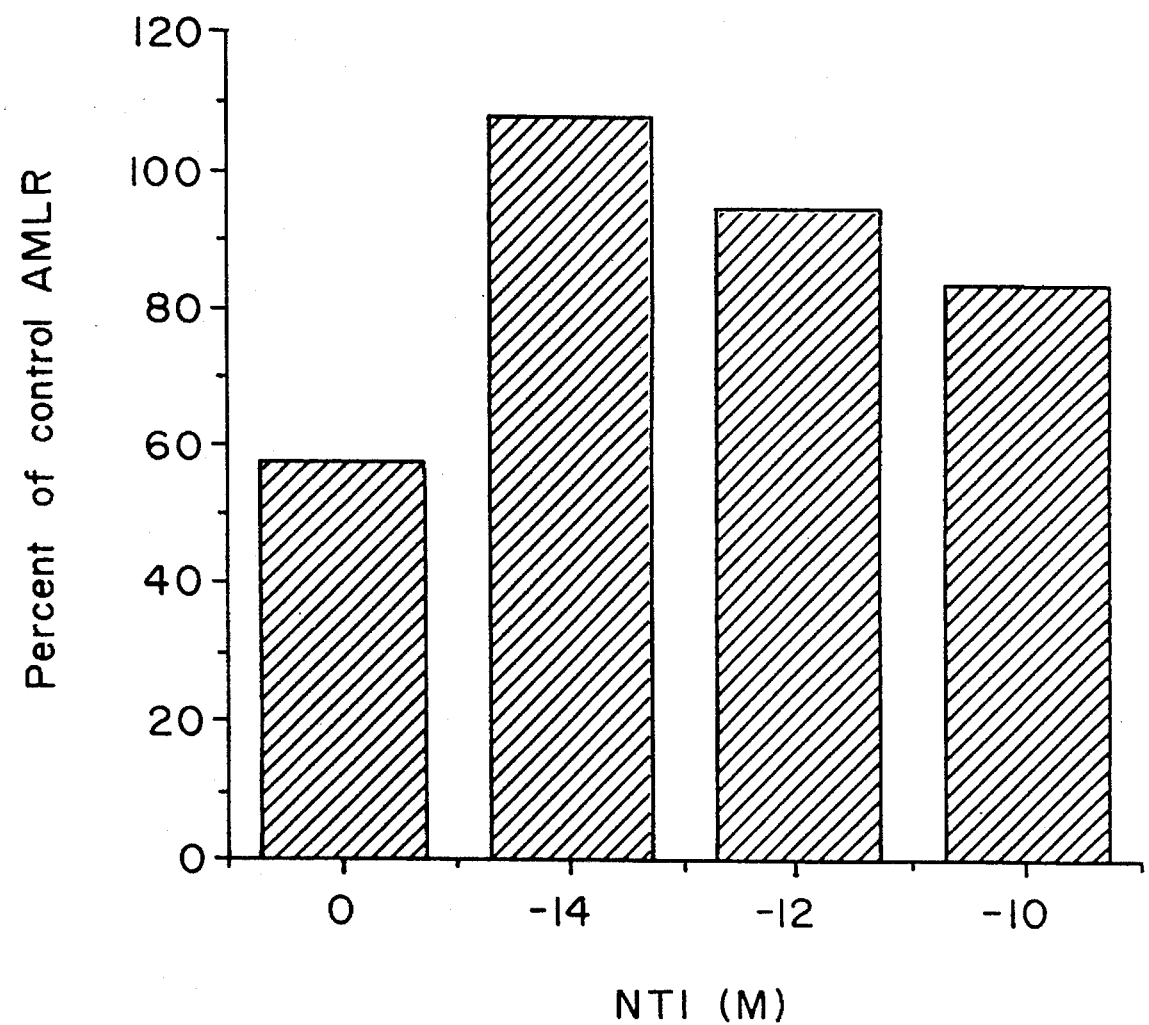

FIGS. 3A and 3B show the reversal of two of the suppressed AMLR cultures by NTI at concentrations ranging form $10^{-10}$ to $10^{-14}$M. FIG. 3A shows the AMLR partially suppressed (20%) in response to CMV at $10^{-2}$; it is completely reversed by NTI at $10^{-12}$ and $10^{-10}$M, but not by NTI at $10^{-14}$M. FIG. 3B shows the AMLR maximally suppressed (42%) in response to CMV $10^{-4}$; again, suppression is reversed completely by NTI at $10^{-4}$M–$10^{-12}$M, and partially by NTI $10^{-10}$M.

Example 5

7-Benzylidene-7-dehydronaltrexone (II, $R^1$=cyclopropyl-methyl, $R^2$=OH, $R^3$=$R^4$=$R^5$=H)

To a stirred solution of naltrexone hydrochloride (200 mg, 0.53 mmol) in MeOH (8 ml) were added sodium hydroxide (1N, 4 ml) and benzaldehyde (0.5 ml, 3.7 mmol) in an ice bath. The mixture was refrigerated for 14 hr. The mixture was neutralized with 1N aqueous HCl and extracted with CHCl$_3$ (3×). The combined organic layers were washed with brine, dried, and concentrated to afford a crude product which was purified on a Sephadex Column (CH-20, MeOH) to give 7-benzylidene-7-dehydronaltrexone (113 mg, 50%): mp 230° C. dec; $R_f$ 0.60 (CHCl$_3$-MeOH-acetone, 19:0.5:0.1); IR (liquid film, cm$^{-1}$) 1685, 1611; MS m/e 429 (M$^+$, EI). Hydrochloride salt: $R_f$ 0.72 (butanol-acetone-H$_2$O, 2:1:1); mp 210° C. dec. Anal. (C$_{27}$H$_{27}$O$_4$N.HCl) C, H, N, Cl.

Example 6

Substituted-7-Benzylidene-7-dehydronaltrexones.

The synthesis of a series of BNTX analogs of formula II were accomplished by aldol condensation of naltrexone with a large excess (30 equivalents) of various substituted benzaldehydes using sodium hydroxide as a base. The reaction of benzylnaltrexone (IV, $R^1$=cyclopropylmethyl, $R^2$=OH, $R^3$=benzyl) with benzaldehyde (1.5 equivalent) using a strong base such as HMDS did not give a desired compound. However, the addition of 12-crown-4 in the reaction mixture gave the desired benzylidene derivative in 48% yield. The cleavage of benzyl ether was accomplished by a treatment with BBr$_3$ in 32% yield. A representative example is presented hereinbelow as Example 6a.

Example 6a.

E-7-(4-Nitrobenzylideno)naltrexone hydrochloride (IIa)

To a solution of naltrexone hydrochloride (100 mg, 0.26 mmol) and 4-nitrobenzaldehyde (1.0 g, 6.6 mmol) in MeOH (40 mL) was added 1N NaOH (2 mL). The mixture was stand for 3 days at 0° C., then diluted with water, acidified with N-HCl and washed with ether. The aqueous layer was made alkaline with sat. aq. NaHCO3 and extracted with EtOAc. The extract was washed with water, dried and evaporated. The residue was chromatographed on silica gel (hexane-EtOAc, 1:1) to afford E-7-(4-nitrobenzylideno)naltrexone (102 mg, 78%). The free base of E-7-(4-nitrobenzylideno)naltrexone was dissolved in ethanol and a few drops of conc. HCl was added. The solution was concentrated and ether was added. The resulting solid was collected, washed with ether, and dried (100 mg). Exact mass calcd. for C$_{27}$H$_{27}$N$_2$O$_6$(M+H)$^+$ 475.1869, found 475.1883. The reaction times (rt=25° C.), yields, and melting points (mp) for analogs IIa–IIm are given on Table V, below.

TABLE V

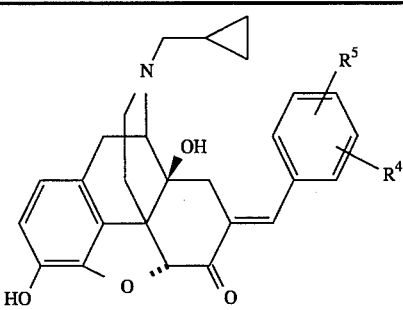

Physical Data for Benzylidenonaltrexone Derivatives

| Compd No | $R^4$ | $R^5$ | mp °C. | Reaction temp., time | Yield (%) |
|---|---|---|---|---|---|
| IIa | p-NO$_2$ | H | 225–235 (decomp) | 0° C. 3 days | 78 |
| IIb | m-NO$_2$ | H | 220–230 (decomp) | 0° C. 3 days | 64 |
| IIc | p-MeO | H | 212–220 (decomp) | rt 7 days | 39 |
| IId | m-MeO | H | 210–225 (decomp) | rt 3 days | 59 |
| IIe | o-MeO | H | 208–215 (decomp) | rt 10 days | 72 |
| IIf | p-Me | H | 222–238 (decomp) | rt 7 days | 33 |
| IIg | p-F | H | 215–225 (decomp) | 0° C. 7 days | 84 |
| IIh | m-F | H | 207–220 (decomp) | rt 1 day | 76 |
| IIi | o-F | H | 215–225 (decomp) | rt 1 day | 57 |
| IIj | o-Cl | H | 210–225 (decomp) | rt 7 days | 48 |
| IIk | p-COOMe | H | 230–238 (decomp) | rt 2 days | 70 |
| III | (2,3-benzo) | | 215–220 (decomp) | rt 5 days | 26 |
| IIM | (3,4-benzo) | | 220–225 (decomp) | rt 5 days | 26 |

Example 7

Bioactivity

The antagonist potencies of compounds of Examples 5 (BNTX) and 6 were compared to the activity of NTI and naltrexone in vitro on the mouse vas deferens (MVD) preparations. Each compound (100 nM) was incubated for 15 min with the tissue prior to adding graded doses of a standard agonist for determination of an IC$_{50}$ value. The standard delta-selective agonist employed was [D-Ala$^2$, D-Leus]enkephalin (DADLE). Concentration-response curves were obtained in the absence (control) and the presence of the antagonist are expressed as IC$_{50}$ values. The IC$_{50}$ ratio represents the IC$_{50}$ in the presence of the antagonist divided by the control IC$_{50}$ value in the same tissue. Therefore, a high IC$_{50}$ ratio represents a correspondingly high degree of antagonism at a particular receptor. The IC$_{50}$ ratios for compounds IIa–c, IIe, IIg–i, IIj, and III–m; determined using the MVD assay are shown in Table VI, below. The IC$_{50}$ ratio is employed to calculate the Ke value using the equation Ke=[antagonist]/(IC$_{50}$ ratio-1). Therefore, a low Ke represents a correspondingly high degree of binding at a particular receptor.

TABLE VI

| Compd No | IC$_{50}$ratio$^a$ (DADLE) | Ke, nM |
|---|---|---|
| IIa | 1.90 | 111 |
| IIb | 5.97 | 20 |
| IIc | 5.52 | 22 |
| IIe | 120 | 0.84 |
| IIg | 2.29 | 77 |
| IIh | 7.87 | 14 |
| IIi | 6.01 | 20 |
| IIj | 130 | 0.76 |
| III | 12.7 | 8.5 |
| IIm | 11.6 | 9.4 |
| NTI | 152 | 0.13 |

$^a$100 nM of each compound, NTI = 20 nM.

The results of these bioassays for BNTX are summarized on Table VII, below.

TABLE VII

Comparison of Opioid Antagonist Potencies in the GPI and MVD Preparations

| | Ke, nM | | | Ke Ratio | |
|---|---|---|---|---|---|
| Antagonist | δ$^a$ | μ$^b$ | κ$^b$ | μ/δ | κ/δ |
| 7-Benzylidene-7-dehydronaltrexone (BNTX) | 2.9 | 8.3 | 100 | 2.9 | 35 |
| NTI$^c$ | 0.13 | 29 | 46 | 223 | 345 |
| Naltrexone | 24 | 1.0 | 5.5 | 0.03 | 0.17 |

$^a$Assayed in the MVD using DADLE as agonist.
$^b$Assayed in the GPI using morphine (μ) and ethylketazocine as agonists.
$^c$δ-selective antagonist (J. Med. Chem., 31, 281 (1988)).

The data shown in Table VII indicate that BNTX is a δ-selective antagonist. It can be noted that its Ke ratios are less than those of the standard δ agonist NTI, but greater than those of naltrexone, a μ-selective antagonist.

While the smooth muscle pharmacological data presented on Table VII reveal that BNTX is δ-selective, the data do not identify its δ subtype selectivity, if any, because it is likely that the MVD preparation contains a different δ subtype or mixture of δ subtypes as compared to the brain.

Therefore, a better assessment of the δ subtype selectivity can be obtained from binding of brain membranes and from antagonism studies in mice. The binding of BNTX to guinea pig brain membranes was determined using the general method of L. L. Werling et al., *J. Pharmacol. Exp. Ther.*, 233, 722 (1985), as modified by A. E. Takemori et al., *J. Pharmacol. Exp. Ther.*, 246, 255 (1988). The radio-ligands employed were [$^3$H]DPDPE ([D-Pen$^2$, D-Pen$^5$]enkephalin) for δ$_1$ receptors, [$^3$H]DSLET([D-Serz-Leus]enkephalin-Thr$^6$) for δ$_2$ receptors, [$^3$H]DAMGO for μ receptors and U69593(trans-(±)-3,4-dichloro-N-methyl-N-[2-(lpyrididinyl)cyclohexyl]benzeneacetamide) for κ receptors.

As shown by the data on Table VIII, below, BNTX exhibited a binding ratio, Ki (δ$_2$)/Ki(δ$_1$) of about 100. Since a high Ki value at a given receptor indicates a lower binding affinity for that receptor, it can be seen that BNTX is highly selective for δ$_1$ receptor sites.

TABLE VIII

BNTX Receptor Selectivity Data

| Standard Antagonist | Selectivity | Smooth Muscle Ke, nM | Binding Ki, nM | $ED_{50}$ Ratio[a] ("Potency Ratio") |
|---|---|---|---|---|
| DADLE | $\delta_1$ | 2.9 | — | — |
| DPDPE | $\delta_1$ | 5.2 | 0.1 | 7.2 |
| DSLET | $\delta_2$ | 2.1 | 10.8 | 0.91 |
| Morphine | μ | 8.3 | — | — |
| DAMGO | μ | — | 13.3 | 0.88 |
| EK | κ | 100 | | |
| U50488H | κ | — | 59 | 1.2 |

[a]$ED_{50}$ of agonist in presence of BNTX/$ED_{50}$ of agonist.

The antagonist effect of BNTX on antinociception was evaluated in mice using the tail flick assay, in accord with the procedure of F. C. Tulunay et al., *J. Pharmacol. Exp. Ther.*, 243, 91 (1987). At least three groups of ten mice were used to generate dose-response curves. A mouse was regarded as positive for antinociception if the latency to flick its tail was more than the control latency plus 3 S.D. of the mean reaction time of the group. The reaction times were determined at the peak time for antinociception after administration of various agonists. Intracerebroventricular (i.c.v.) injections were made in a volume of 5 μl by the method of T. J. Haley et al., *Br. J. Pharmacol.*, 12, 12 (1957).

On Table VIII, the potencies are expressed as $ED_{50}$ ratios, which represent the $ED_{50}$ of the standard agonist administered subcutaneously in the presence of BNTX (6.25 pmol/i.c.v./mouse), divided by the $ED_{50}$ of the standard agonist. Thus, the dose-response curve obtained for DPDPE was shifted by a factor of about 7.2 to higher concentration, while the curves of DSLET, morphine and U50488H (κ agonist) were not shifted significantly. Therefore, the binding data determined on guinea pig brain membranes, correlate with the in vivo data, and are superior to the smooth muscle-based assays data shown in Table IX, as an indicator of δ subtype selectivity. It is believed that BNTX is the first $\delta_1$ opioid receptor subset-selective antagonist to be identified.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating a viral infection selected from the group consisting of coronavirus and cytomegalovirus characterized by a depressed autologous mixed lymphocyte response (AMLR) comprising administering to a mammal in need of such treatment an amount of a compound of the formula I:

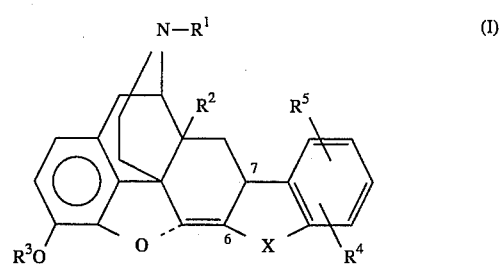

wherein $R^1$ is $(C_1-C_5)$alkyl, $C_3-C_6$(cycloalkyl)alkyl, $C_5-C_7$(cycloalkenyl)alkyl, aryl, aralkyl, trans $(C_4-C_5)$alkenyl, allyl or furan-2-ylalkyl, $R^2$ is H, OH or $O_2C(C_1-C_5)$alkyl; $R^3$ is H, $(C_1-C_5)$alkyl; or $((C_1-C_5)$alkyl)-CO; $R^4$ and $R^5$ are individually H, F, Cl, Br, NCS, $NO_2$, $NH_2$, $(C_1-C_5)$alkyl or $(C_1-C_5)$alkoxy, or together are benzo; and X is O, S or NY, wherein Y is H, $(C_1-C_5)$alkyl or benzyl; and the pharmaceutically acceptable salts thereof; wherein said amount is effective to elevate the AMLR of said mammal.

2. The method of claim 1 wherein the mammal is a human.

3. The method of claim 1 wherein $R^1$ is $C_3-C_6$-(cycloalkyl)alkyl and $R^2$=OH.

4. The method of claim 3 wherein $R^3$ is H.

5. The method of claim 4 wherein $R^1$ is cyclopropylmethyl.

6. The method of claim 1 wherein X is NH, O or (benzyl)N.

7. The method of claim 1 wherein $R^4$ and $R^5$ are H.

8. The method of claim 1 wherein the compound of formula I is naltrindole.

9. The method of claims 1 or 2 comprising administering the amount of the compound of formula I in a unit dosage form in combination with a pharmaceutically acceptable carrier.

10. The method of claim 9 wherein the pharmaceutically acceptable carrier is a liquid.

11. The method of claim 9 wherein the unit dosage form comprises a tablet, capsule or solution comprising the compound of formula I.

12. The method of claims 1 or 2 wherein the amount of the compound of formula I is administered parenterally.

13. The method of claim 12 wherein the amount of the compound of formula I is administered by injection or by intravenous infusion.

14. The method of claim 12 wherein the amount of the compound of formula I is administered transdermally.

15. The method of claims 1 or 2 wherein the amount of the compound of formula I is administered orally.

* * * * *

UNITED STATES PATENT AND TRADEMARK OFFICE
CERTIFICATE OF CORRECTION

PATENT NO. : 5,464,841
DATED : November 7, 1995
INVENTOR(S) : Philip S. Portoghese, et al It is certified that error appears in the above-indentified patent and that said Letters Patent is hereby corrected as shown below:

Title page, item [73] [Assignee] please insert --"Regents of the University of Minnesota, Minneapolis, Minn"-- therefor.

Item [76]   [Inventors] should read "Philip S. Portoghese, St. Paul, Minn"

Item [76],  [Inventors] should read "Burt M. Sharp, St. Louis Park, Minn"

Item [76],  [Inventors] should read "Kristin M. Linner, St. Paul, Minn"

Column 7 Line 46 "(mixture)" should read --(mixture)--therefor.
Column 7, Line 56 "1-18" should read --1-18--.
Column 7 Line 56 "(1-7, 9-15)" should read --(1-7, 9-15)-- therefor.

Column 7 Line 57 "(8), benzopyrazine (16), benzoquinoline (17)" should read --(8), benzopyrazine, (16) benzoquinoline (17)-- therefor.

Column 7 Line 58 "(18)" should read --(18)-- therefor.

Column 9 Line 14 "1-7, 9-15 and 18" should read --1-7, 9-15 and 18-- therefor.

Column 9 Line 20 "(30)" should read --(30)-- therefor.

Column 9 Line 24 "(6)" and "12a" should read --(6)--and--12a-- therefor.

Column 9 Line 25 "12b" should read --12b-- therefor.

__UNITED STATES PATENT AND TRADEMARK OFFICE__
CERTIFICATE OF CORRECTION

PATENT NO. : 5,464,841  
DATED : November 7, 1995  
INVENTOR(S) : Philip S. Portoghese, et al Page 2 of 3

It is certified that error appears in the above-indentified patent and that said Letters Patent is hereby corrected as shown below:

Column 9 Line 27 "(18)" should read --(<u>18</u>)-- therefor.

Column 9 Line 28 "8" should read --<u>8</u>-- therefor.

Column 9 Line 30 "IVa.HCl," should read --<u>IVa</u>·HCl-- therfor.

Column 9 Line 31 "(31)" should read --(<u>31</u>)-- therefor.

Column 9 Line 31 "0-phenylhydroxylamine.HCl" should read --<u>0-</u>phenylhydroxylamine·HCl-- therefor.

Column 9 Line 33 "16" should read --<u>16</u>-- therfor.

Column 9 Line 33 "IVa.HCl" should read --<u>IVa</u>·HCl-- therefor.

Column 9 Line 34 "21" should read --<u>21</u>-- therefor.

Column 9 Line 35 "25" should read --<u>25</u>-- therefor.

Column 9 Line 36 "17" should read --<u>17</u>-- therefor.

Column 9 Line 37 "naltrexone.HCl" should read --naltrexone·HCI-- therefor.

UNITED STATES PATENT AND TRADEMARK OFFICE
CERTIFICATE OF CORRECTION

PATENT NO. : 5,464,841
DATED : November 7, 1995
INVENTOR(S) : Philip S. Portoghese, et al It is certified that error appears in the above-indentified patent and that said Letters Patent is hereby corrected as shown below:

Column 9 Line 37 "28" should read --$\underline{28}$-- therefor.

Column 9 Line 63 "1-12 and 13-17" should read --$\underline{1}$-$\underline{12}$ and $\underline{13}$-$\underline{17}$-- therefor.

Column 10 Line 41 "naltrexone.HCl" should read --naltrexone·HCl-- therefor.

Column 12 Line 37 "$ED^d$" should read --$Ek^d$-- therefor.

Column 17 Line 38 "IIM" should read --IIm-- therefor.

Signed and Sealed this

Tenth Day of September, 1996

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,464,841
DATED : November 7, 1995
INVENTOR(S) : Phillip S. Portoghese et al.

It is certified that error appears in the above-indentified patent and that said Letters Patent is hereby corrected as shown below:

Title Page [Assignee] please insert --"Regents of the University of Minnesota, Minneapolis, Minn" and Minneapolis Medical Research Foundation, Minneapolis, Minn-- therefor.

Signed and Sealed this

Twelfth Day of November, 1996

Attest:

BRUCE LEHMAN

*Attesting Officer*     *Commissioner of Patents and Trademarks*